US00PP35846P2

(12) United States Plant Patent
Carr

(10) Patent No.: US PP35,846 P2
(45) Date of Patent: May 28, 2024

(54) ***LAVANDULA* PLANT NAMED 'HILLAV'**

(50) Latin Name: ***Lavandula* X *intermedia***
Varietal Denomination: Hillav

(71) Applicants: Hillier Nurseries, Romsey (GB); Lloyd Traven, Kintnersville, PA (US)

(72) Inventor: Charles Carr, Romsey (GB)

(73) Assignees: HILLIER NURSERIES LTD, Romsey (GB), part interest; Lloyd Traven, Kintnersville, PA (US), part interest ( * ) Notice: Subject to any disclaimer, the term of this patent is extended or adjusted under 35 U.S.C. 154(b) by 0 days.

(21) Appl. No.: 18/370,713

(22) Filed: Sep. 20, 2023

(30) Foreign Application Priority Data

May 5, 2023 (QZ) ..... PBR 20230975

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./263.1, 445
See application file for complete search history.

*Primary Examiner* — Karen M Redden
(74) *Attorney, Agent, or Firm* — Penny J. Aguirre

(57) ABSTRACT

A new cultivar of *Lavandula* plant named 'Hillav' that is characterized by its foliage that is bright silvery in color that is retained throughout the growing season, its broad, thick leaves, its upright, well-branched plant habit, its large and dense flower panicles with a desirable fragrance, its flowers that are white in color, its flower stems that are long and strong, its re-blooming and a long flowering period, its strong root system, its clean foliage and appears to lack senstivity to leaf and root diseases, its good winter hardiness and drought and heat resistance, its suitability for use as a garden plant, container plant and cut flowers, its attraction to pollinators, and its ease of growing.

2 Drawing Sheets

Botanical classification: *Lavandula* X *intermedia*.
Variety denomination: 'Hillav'.

CROSS REFERENCE TO A RELATED APPLICATION

This application claims priority to European Community Plant Variety Office (CPVO) Plant Breeder's Rights Application No. 2023/0975, filed on May 5, 2023, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Lavandula* X *intermedia* and will be referred to hereafter by its cultivar name, 'Hillav'. 'Hillav' is a new variety of Lavender plant suitable for use as a landscape, container, and cut flower.

The new cultivar was selected by the Inventor as a seedling found in a container block that had been planted with open-pollinated seeds of *Lavandula* 'Niko' (U.S. Plant Pat. No. 24,193) in 2018 in a nursery in Romsey, United Kingdom. The male parent is unknown.

Asexual propagation of the new cultivar was first accomplished by the Inventor by stem cuttings in 2018 in Romsey, United Kingdom. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hillav' as a unique cultivar of *Lavandula*.

1. 'Hillav' exhibits foliage that is bright silvery in color that is retained throughout the growing season.
2. 'Hillav' exhibits broad, thick leaves.
3. 'Hillav' exhibits an upright, well-branched plant habit.
4. 'Hillav' exhibits large and dense flower panicles with a desirable fragrance.
5. 'Hillav' exhibits flowers that are white in color.
6. 'Hillav' exhibits flower stems that are long and strong.
7. 'Hillav' exhibits re-blooming and a long flowering period.
8. 'Hillav' exhibits a strong root system.
9. 'Hillav' exhibits clean foliage and appears to lack senstivity to leaf and root diseases.
10. 'Hillav' exhibits good winter hardiness and drought and heat resistance.
11. 'Hillav' exhibits suitability for use as a garden plant, container plant and cut flowers.
12. 'Hillav' exhibits attraction to pollinators.
13. 'Hillav' exhibits ease of growing.

The female parent of 'Hillav' differs from 'Hillav' in having a smaller plant size, smaller leaves, a different flower form, and flowers that are purple in color. 'Hillav' can also be compared to the *Lavandula* cultivar 'Arctic Snow' (not patented). 'Arctic Snow' is similar to 'Hillav' in having white flowers. 'Arctic Snow' differs from 'Hillav' in having a more compact plant habit, shorter stems, and smaller flowers.

BRIEF DESCRIPTION OF THE DRAWINGS

The accompanying colored photographs illustrate the overall appearance and distinct characteristics of a two-year-old plant of the new *Lavandula* as grown outdoors in a 14-cm container in 2018 in Romsey, The United Kingdom.

The photograph in FIG. 1 illustrates the plant habit of 'Hillav' in bloom.

Figure 1:
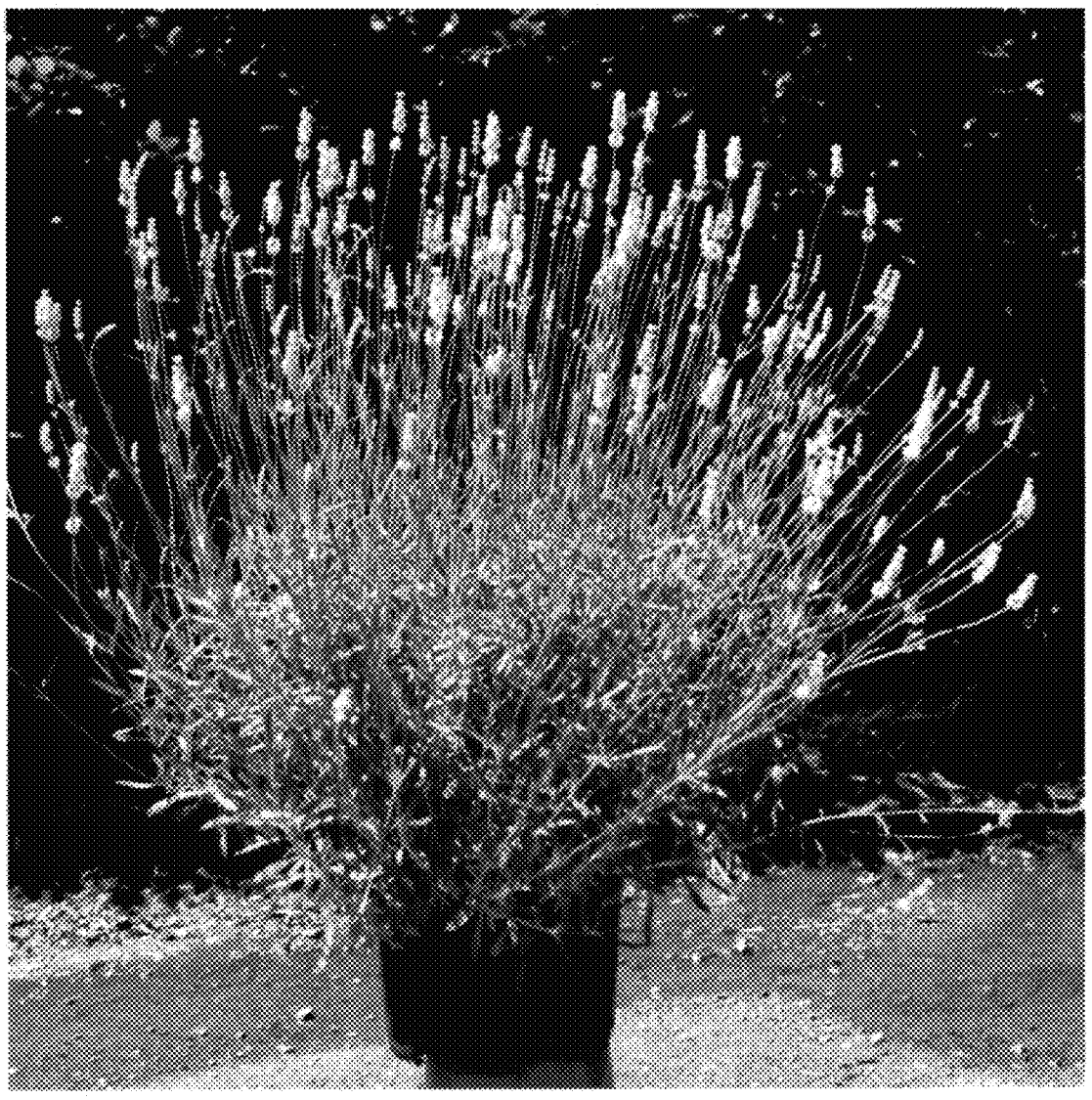
Figure 2:
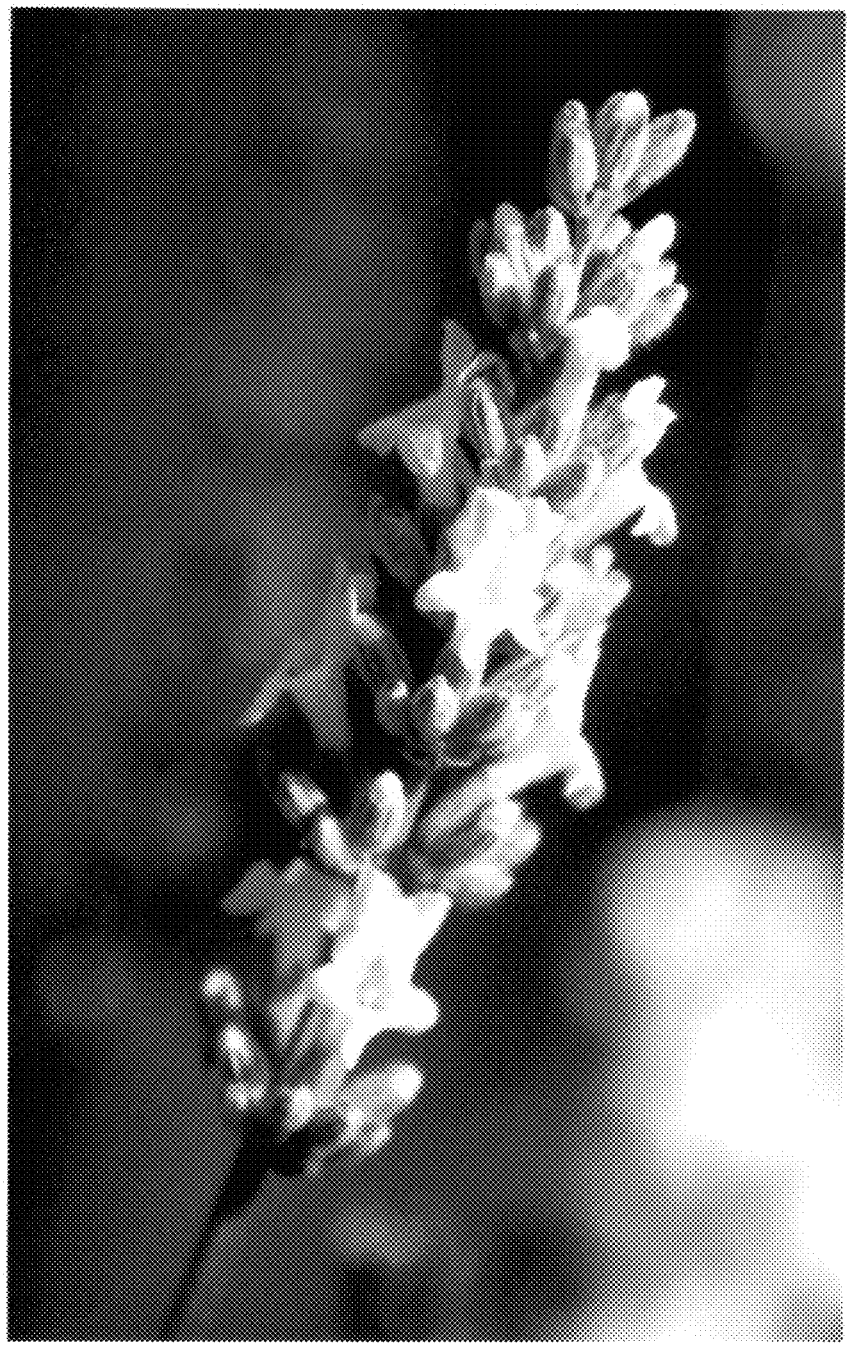

The photograph in FIG. 2 provides a close up view of an inflorescence of 'Hillav'.

The colors in the photographs are as close as possible with the digital photography techniques utilized and the color values cited in the detailed botanical description accurately describe the colors of the new *Lavandula*.

DETAILED BOTANICAL DESCRIPTION

The following is a detailed description of 2.5-year-old plants of the new cultivar as field grown in Lier, Belgium. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Reblooms from June to October in Belgium.

*Plant type.*—Herbaceious perennial.

*Plant habit.*—Upright mound, bushy, with strong flowering stems held above foliage.

*Height and spread.*—Reaches 1 m in height, 82 cm in spread as a 2.5-year-old plant in the landscape.

*Cold hardiness.*—At least in U.S.D.A. Zone 5.

*Diseases and pests.*—Has been observed to be free of leaf and root diseases; however resistance to specific pathogens has been identified, no susceptibility or resistant to pests has been observed.

*Root description.*—Fine and fibrous, 165B in color.

*Root development.*—8 to 10 weeks, time from rooted plant to P9 12 to 16 weeks from RC to P9.

*Propagation.*—Stem cuttings.

*Growth.*—Vigorous.

Stem description:

*Stem shape.*—Square.

*Stem color.*—Young; 138B, mature wood at base; 165A.

*Stem surface.*—Moderately tomentose.

*Stem size.*—Up to 58 cm in length, 3 mm in diameter.

*Stem strength.*—Strong.

*Stem aspect.*—Outward to vertical.

*Branching.*—Basal, 20 branches.

*Internode length.*—3 cm.

Foliage description:

*Leaf shape.*—Narrowly oblong.

*Leaf division.*—Simple.

*Leaf base.*—Cuneate.

*Leaf apex.*—Acute.

*Leaf venation.*—Pinnate, color; insignificant.

*Leaf margins.*—Entire and revolute.

*Leaf arrangement.*—Opposite.

*Leaf attachment.*—Sessile.

*Leaf number.*—Average of 10 to 12 per stem.

*Leaf surface.*—Both surfaces lightly pubescent.

*Leaf size.*—8 cm in length, 8 mm in width.

*Leaf color.*—Young upper and lower surface; 133C to 133D, mature upper surface; 137C, mature lower surface; 137D.

*Leaf fragrance.*—Strong *Lavandula* scent.

Inflorescence description:

*Inflorescence type.*—Terminal.

*Inflorescence shape.*—Cylindrical.

*Inflorescence number.*—1 Spike per flowering stem.

*Inflorescence fragrance.*—Strong Lavender fragrance.

*Lastingness of inflorescence.*—Average of 3 weeks with open flowers, flowers last an average of 2 days.

*Inflorescence size.*—7.7 cm in length, 2.5 cm in width.

*Flower buds.*—Average of 8 mm in length, 3 mm in diameter, ovate in shape, glabrous surface, N155D in color.

*Flowers.*—Persistant, labiate in shape, 6 mm in length, 7 mm in diameter.

*Petals.*—Ligulate in shape, both surfaces glabrous, entire margins, obsture apex, fused base, upper lip 4.4 cm in length, 5 mm in width, lower lips 2 mm in length, 7 mm in width, color when opening and fully open upper and lower surface N155D.

*Calyx.*—Fused, 5 mm in length, 3 mm in diameter.

*Peduncles.*—Strong, 26 cm in length, 2.5 mm in width, 138B in color, surface is slightly pubescent.

Reproductive organs:

*Pistils.*—1, 8 mm in length, stigma; reniform in shape, 155A in color, style; 6 mm in length, NN155C in color, ovary; 137B in color.

*Stamens.*—5, anthers; ovate in shape, 1 mm in length, 12B in color, filament; 3 mm in length, NN155D in color, pollen; moderate in quantity, 12B in color.

*Seeds.*—No seeds observed to date.

It is claimed:

1. A new and distinct cultivar of *Lavandula* plant named 'Hillav' as herein illustrated and described.

* * * * *